United States Patent
Ho

(10) Patent No.: US 9,138,529 B2
(45) Date of Patent: Sep. 22, 2015

(54) ANTICOAGULANT-FREE DIALYSIS SYSTEMS AND METHODS

(75) Inventor: Chih-Hu Ho, Farmington, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 376 days.

(21) Appl. No.: 13/640,579

(22) PCT Filed: Apr. 14, 2011

(86) PCT No.: PCT/US2011/032519
§ 371 (c)(1),
(2), (4) Date: Oct. 11, 2012

(87) PCT Pub. No.: WO2011/130528
PCT Pub. Date: Oct. 20, 2011

(65) Prior Publication Data
US 2013/0035663 A1   Feb. 7, 2013

Related U.S. Application Data

(60) Provisional application No. 61/324,570, filed on Apr. 15, 2010.

(51) Int. Cl.
*A61M 1/36* (2006.01)
*A61M 1/34* (2006.01)
(Continued)

(52) U.S. Cl.
CPC ............ *A61M 1/3672* (2013.01); *A61K 31/722* (2013.01); *A61K 31/734* (2013.01);
(Continued)

(58) Field of Classification Search
CPC ....... A61M 1/16; A61M 1/34; A61M 1/3455; A61M 1/3672; A61M 1/3679; B01D 2323/04; B01D 2323/30; B01D 2325/38; B01D 61/28; B01D 67/0093; B01D 71/68; B01D 71/76; C02F 1/44; A61K 31/722; A61K 31/734
See application file for complete search history.

(56) References Cited

U.S. PATENT DOCUMENTS

| 3,740,421 A | 6/1973 | Schmolka et al. |
| 6,524,482 B2 | 2/2003 | Bruening et al. |

(Continued)

FOREIGN PATENT DOCUMENTS

WO   WO 2007/062197 A1   5/2007

OTHER PUBLICATIONS

Notification of Transmittal of the International Search Report and the Written Opinion of the International Searching Authority for International Application No. PCT/US2011/032519 filed Apr. 14, 2011.
(Continued)

*Primary Examiner* — John Kim
(74) *Attorney, Agent, or Firm* — Hamilton, Brook, Smith & Reynolds, P.C.

(57) ABSTRACT

An extracorporeal blood treatment system includes means for withdrawing blood from a patient, and means for transporting the blood through a calcium trap. The calcium trap includes a substrate having an immobilized species, the species being adapted to reduce the calcium concentration in the blood to a concentration that prevents blood clotting in the extracorporeal blood treatment system, thereby producing calcium-depleted blood. The extracorporeal blood treatment system also includes means for treating the calcium-depleted blood downstream of the calcium trap by an extracorporeal blood treatment device, thereby producing treated calcium-depleted blood, means for infusing calcium into the treated calcium-depleted blood downstream of the extracorporeal blood treatment device to add calcium to the treated calcium-depleted blood, and means for returning treated blood back to the patient.

18 Claims, 4 Drawing Sheets

(51) Int. Cl.
*B01D 71/76* (2006.01)
*B01D 61/30* (2006.01)
*A61K 31/722* (2006.01)
*A61K 31/734* (2006.01)
*B01D 61/28* (2006.01)
*B01D 67/00* (2006.01)
*B01D 71/68* (2006.01)
*A61M 1/16* (2006.01)
*C02F 1/44* (2006.01)

(52) U.S. Cl.
CPC ........... *B01D 61/28* (2013.01); *B01D 67/0093* (2013.01); *B01D 71/68* (2013.01); *B01D 71/76* (2013.01); *A61M 1/16* (2013.01); *A61M 1/34* (2013.01); *A61M 1/3455* (2013.01); *A61M 1/3679* (2013.01); *B01D 2323/04* (2013.01); *B01D 2323/30* (2013.01); *B01D 2325/38* (2013.01); *C02F 1/44* (2013.01)

(56) References Cited

U.S. PATENT DOCUMENTS

| | | | |
|---|---|---|---|
| 6,662,805 B2 * | 12/2003 | Frondoza et al. | 128/898 |
| 2003/0148017 A1 | 8/2003 | Tuominen et al. | |
| 2005/0061742 A1 | 3/2005 | Brady et al. | |
| 2010/0096330 A1 | 4/2010 | Gotch et al. | |

OTHER PUBLICATIONS

Daugirdas, J.T. et al., Handbook of Dialysis, pp. 204-251 (2007).

Notification Concerning Transmittal of International Preliminary Report on Patentability and the Written Opinion of the International Searching Authority for International Application No. PCT/US2011/032519 filed Apr. 14, 2011; Date of Mailing Oct. 26, 2012.

* cited by examiner

ANTICOAGULANT-FREE DIALYSIS SYSTEMS AND METHODS

This application is the U.S. National Stage of International Application No. PCT/US2011/032519, filed Apr. 14, 2011, which designates the U.S., published in English, and claims the benefit of U.S. Provisional Application No. 61/324,570, filed on Apr. 15, 2010. The entire teachings of the aforementioned application are incorporated herein by reference.

BACKGROUND OF THE INVENTION

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites including urea, creatinine, and uric acid accumulate in the body's tissues, which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. Typically, the blood passes through the inside of semi-permeable hollow fibers, and the dialysis solution (dialysate) flows on the outside of the semi-permeable hollow fibers in a countercurrent direction. The waste and toxins dialyze out of the blood through the semi-permeable membrane into the dialysis solution, which can then be discarded.

The patient's blood is typically exposed to intravenous cannulas, tubing, drip chambers, headers, potting compound, and dialysis membranes during the dialysis procedure. These surfaces exhibit a variable degree of thrombogenicity and can initiate clotting of blood, especially in conjunction with exposure of blood to air in drip chambers. The resulting thrombus formation may be significant enough to cause occlusion and malfunction of the extracorporeal circuit. See J. T. Daugirdas, P. G. Blake, and T. S. Ing, *Handbook of Dialysis*, (2007).

One method of preventing blood clotting is to administer an anticoagulant, typically heparin, to the patient, shortly before or during the dialysis treatment. Heparin, however, has potential undesirable side effects, such as, for example, pruritus, allergy, osteoporosis, hyperlipidemia, heparin-induced thrombocytopenia (HIT), and excessive bleeding. Heparin is therefore not recommended for patients at risk of bleeding due to gastrointestinal lesions (gastritis, peptic ulcer, angiodysplasia), recent surgery, or pericarditis.

Another method of preventing blood clotting is by regional citrate anticoagulation (RCA), which can be used alone or combined with potentially reduced heparin administration, as shown in FIG. 1. Id. at p. 221. The application of RCA in hemodialysis typically involves infusion of citrate (e.g., tri-sodium citrate) before the hemodialyzer, which complexes with ionized calcium (iCa) in the blood and thereby interferes with the blood coagulation cascade by removing calcium (formerly known as factor IV) from the blood, preventing the blood from clotting, followed by calcium infusion after the dialyzer. The extremely low ionized calcium levels generated by infusion of citrate into the arterial line prevent clotting in the extracorporeal circuit but have to be raised again in the venous line before the blood re-enters the patient's systemic circulation. Citrate infusion and calcium replacement have to be balanced carefully to avoid systemic hypo- or hypercalcemia in the patient. See U.S. application Ser. No. 12/580,803, entitled "Method Of Determining A Phosphorus Binder Dosage For A Dialysis Patient," filed on Oct. 16, 2009. This balance is typically achieved by close monitoring of systemic iCa levels, which is generally accomplished by repetitive blood draws and iCa measurements throughout the dialysis treatment. This is a labor- and material-intensive process and, hence, an undesirable cost factor. Furthermore, the introduction of citrate into the blood is not recommended for patients with liver disease, due to their diminished ability to process free citrate and citrate-calcium complexes.

Therefore, there is a need for a method of preventing blood from clotting in an extracorporeal blood treatment system without addition of an anticoagulant into the blood.

SUMMARY OF THE INVENTION

The invention generally is directed to an extracorporeal blood treatment system including a calcium trap comprising a substrate having an immobilized species, the species being adapted to reduce the calcium concentration in the blood to a concentration that prevents blood clotting in the extracorporeal blood treatment system.

In one embodiment, an extracorporeal blood treatment system includes means for withdrawing blood from a patient, and means for transporting the blood through a calcium trap. The calcium trap includes a substrate having an immobilized species, the species being adapted to reduce the calcium concentration in the blood to a concentration that prevents blood clotting in the extracorporeal blood treatment system, thereby producing calcium-depleted blood. The extracorporeal blood treatment system also includes means for treating the calcium-depleted blood downstream of the calcium trap by an extracorporeal blood treatment device, thereby producing treated calcium-depleted blood, means for infusing calcium into the treated calcium-depleted blood downstream of the extracorporeal blood treatment device to add calcium to the treated calcium-depleted blood, and means for returning treated blood back to the patient. In some embodiments, the substrate in the calcium trap is selected from the group consisting of polysulfone hollow fiber membranes, silica beads, polystyrene beads, hydrogel beads, or any combination thereof. In certain embodiments, the substrate in the calcium trap comprises polystyrene beads. In a specific embodiment, the polystyrene beads are crosslinked polystyrene beads. In certain other embodiments, the substrate in the calcium trap comprises hydrogel beads. The hydrogel beads can include one of chitosan, crosslinked chitosan, positively charged chitosan, or any combination thereof. In some embodiments, the immobilized species is selected from the group consisting of ethylene diamine tetraacetic acid (EDTA), citrate, alginate, or calcium-binding protein. In a specific embodiment, the immobilized species comprises alginate.

In some embodiments, the extracorporeal blood treatment device can include dialysis, adsorption, and/or filtration. In a specific embodiment, the extracorporeal blood treatment system can include a dialyzer. The dialyzer can include a hydrophobic membrane, wherein at least one copolymer is attached to the hydrophobic membrane, and wherein each copolymer is comprised of at least one hydrophobic segment and at least one hydrophilic segment. In some embodiments, calcium is added to the calcium-depleted blood to adjust the patient's intradialytic calcium mass balance to desired levels relative to the patient's interdialytic intakes of calcium and liquid.

The invention is also directed to a method of dialyzing blood comprising directing blood into a dialysis system including a dialyzer, and directing the blood through a calcium trap located upstream of the dialyzer. The blood can be blood of a patient undergoing dialysis. The calcium trap includes a substrate having an immobilized species, the species being adapted to reduce the calcium concentration in the blood to a concentration that prevents blood clotting in the dialysis system, thereby producing calcium-depleted blood. The method further includes directing the calcium-depleted blood through the dialyzer, thereby removing deleterious substances and aqueous fluid from the blood, and infusing a calcium containing solution into the calcium-depleted blood. Infusing the calcium containing solution can be to adjust a patient's intradialytic calcium mass balance to desired levels relative to the patient's interdialytic intakes of calcium and fluid. The method can further include directing the blood back to the patient. In a specific embodiment, maintaining or adjusting a patient's intradialytic calcium mass balance to desired levels relative to the patient's interdialytic intakes of calcium and liquid includes determining a desired calcium mass balance for the patient over a complete dialysis cycle, calculating an intradialytic calcium mass balance, and adjusting the calcium concentration in the calcium containing solution.

This invention has many advantages, including reducing blood clotting in the extracorporeal blood treatment system without introducing an anticoagulant into the blood, thereby reducing the risk of occlusion and malfunction of the extracorporeal blood treatment system while avoiding potential negative side effects of anticoagulants on the patient's health.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
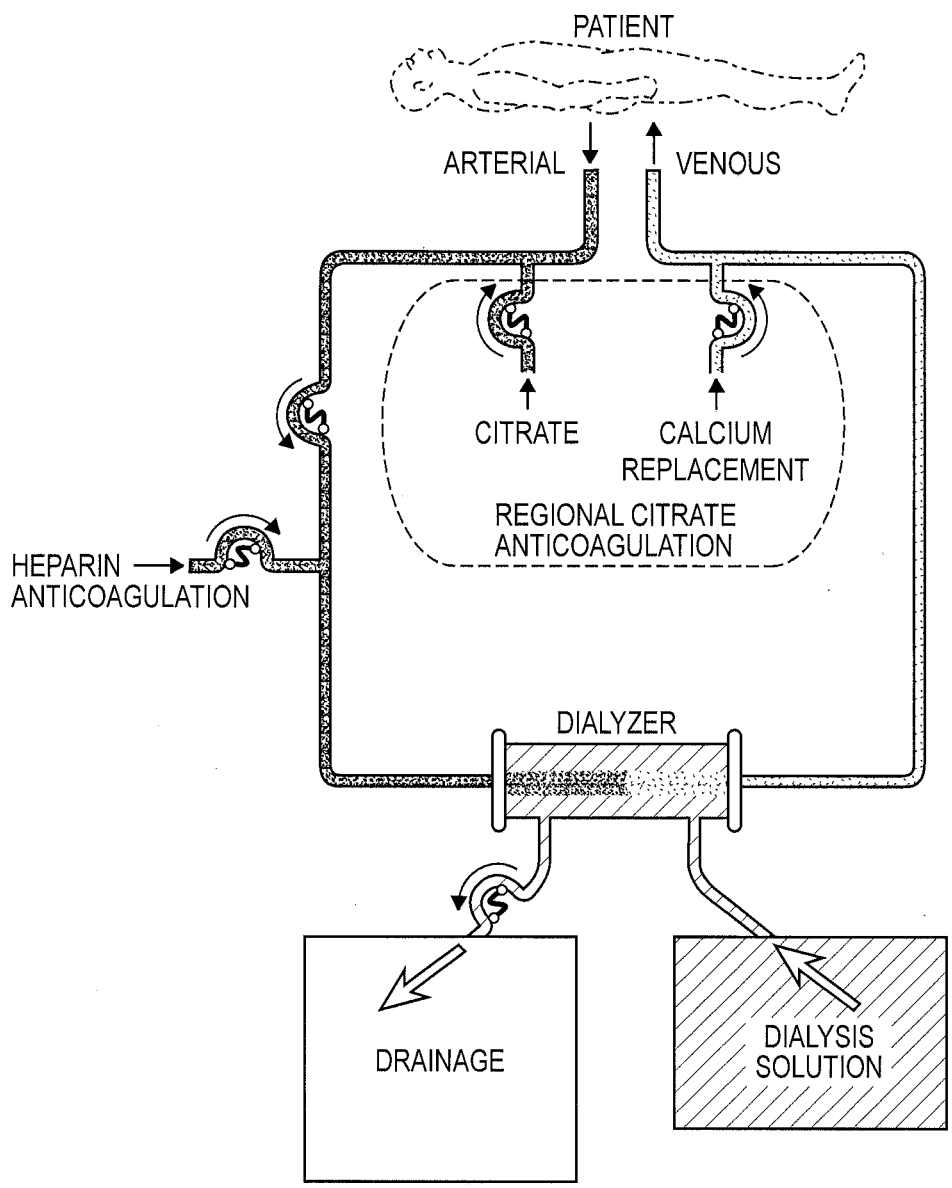
FIG. 1 is an illustration of a prior art extracorporeal blood treatment system employing regional citrate anticoagulation.
Figure 2:
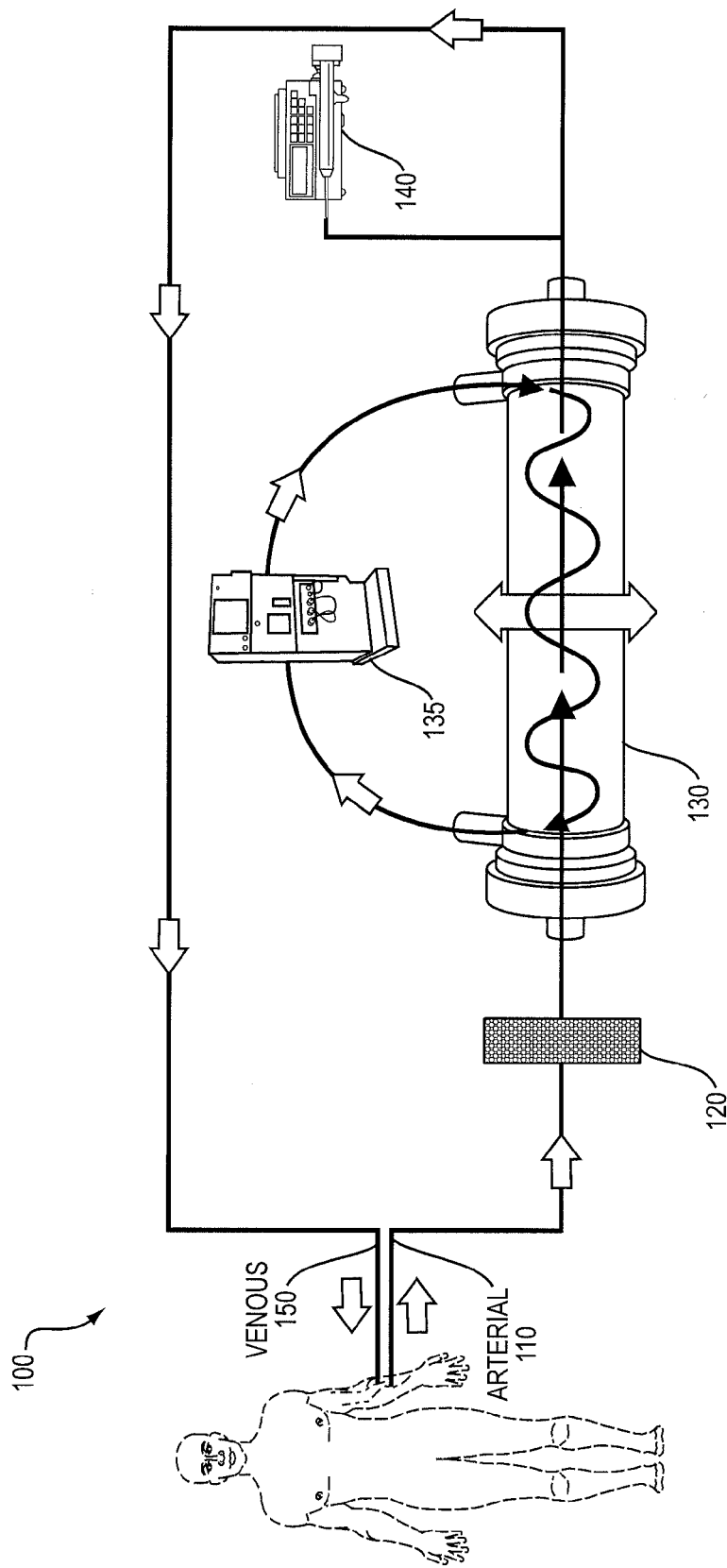
FIG. 2 is an illustration of an extracorporeal blood treatment system employing a calcium trap according to the invention.

In one embodiment, shown in FIG. 2, an extracorporeal blood treatment system 100 includes means 110 for withdrawing blood from a patient, such as a large bore dialysis needle (not shown), or a separate dialysis access device that connects to the patient's arterial system. The access device (not shown) includes a short tubular section, adapted at one end for connecting to an open end of the extracorporeal blood circuit tubing, and at the other end having a large bore dialysis needle for accessing the patient's arterial blood. Either or both of the extracorporeal blood circuit tubing and the access devices may include flow shut-off clamps and liquid access devices that have injection/administration port structures. The port structures provide mechanisms through which a dialysis administrator can, for example, safely access the arterial blood flow to remove samples of the patient's blood or inject drugs or liquids.

The extracorporeal blood treatment system 100 further includes means, such as extracorporeal blood circuit tubing, for transporting the blood through a calcium trap 120. The tubing can be made of biocompatible polymers, such as, for example, polyvinyl chloride (PVC).

The calcium trap 120 includes a substrate having an immobilized species, the species being adapted to reduce the ionized calcium (iCa) concentration in the blood to a concentration that prevents blood clotting in the extracorporeal blood treatment system, thereby producing calcium-depleted blood. The target iCa concentration before the blood treatment device 130 is typically in a range of between about 0.1 mmol/liter and about 0.4 mmol/liter.

The substrate contained in calcium trap 120 can be selected from the group consisting of polysulfone hollow fiber membranes, silica beads, polystyrene beads, such as crosslinked polystyrene beads, or hydrogel beads, or any combination thereof. The hydrogel beads can include one of chitosan, crosslinked chitosan, positively charged chitosan, or any combination thereof. The calcium-trapping species immobilized on the substrate can be selected from the group consisting of ethylene diamine tetraacetic acid (EDTA), citrate, alginate, or calcium-binding proteins, such as, for example, calmodulin or calsequestrin.

In a specific embodiment, the calcium trap 120 can be made by mixing alginate with chitosan to form a chitosan-alginate solution. A chitosan hydrogel can be made by lowering the pH of the solution to below about pH 5, or by adding a crosslinking reagent, such as, for example, glutaraldehyde, to form crosslinks between chitosan molecules by reaction of the glutaraldehyde with the primary amine group on the chitosan. The hydrogel can be extruded to form beads to fill calcium trap 120.

In another embodiment, the calcium trap 120 can be filled with beads made by mixing alginate with copolymers that have a hydrophobic segment and a hydrophilic segment, such as polyethylene oxide-polypropylene oxide-polyethylene oxide triblock copolymers that are commercially available under the registered trademark PLURONIC®. (BASF, Wyandotte, Mich.). See application Ser. No. 10/013,323 of O. Tuominen et al., published as U.S. 2003/0148017 on Aug. 7, 2003, and U.S. Pat. No. 3,740,421 issued to I. R. Schmolka on Jun. 19, 1973. The solution is then treated with electron beam irradiation to induce crosslinking. The resulting hydrogel can be formed into beads to fill calcium trap 120. In another embodiment, hollow fiber polysulfone membranes, such as those employed in high flux dialyzers, can be treated with alginate solution to form a thin layer of alginate on the lumen side (i.e., inside) of the hollow fibers. The treated hollow fibers can be used in calcium trap 120.

The extracorporeal blood treatment system 100 also includes means for treating the calcium-depleted blood downstream of the calcium trap by an extracorporeal blood treatment device 130, thereby producing treated calcium-depleted blood. The blood treatment device 130 can include dialysis, adsorption, and filtration. In a specific embodiment, the blood treatment device can include a dialyzer. Such means can be a dialyzer 130, shown in FIG. 2, that includes a pump 135 for flowing dialysate countercurrently over the outside of semi-permeable hollow fiber membranes of dialyzer 130. The dialyzer 130 can be, for example, a high flux dialyzer, such as an Optiflux® F180NR dialyzer (Fresenius Medical Care, North America, Waltham, Mass.).

As shown in FIG. 2, the extracorporeal blood treatment system 100 further includes means 140 for infusing calcium into the treated calcium-depleted blood downstream of the extracorporeal blood treatment device 130 to add calcium to the treated blood. Means 140 can be a calcium infusion syringe, typically charged with about 550 mmol/liter calcium chloride ($CaCl_2$) solution. The solution can be added at a rate in a range of between about 20 ml/hr and about 30 ml/hr. In one embodiment, the calcium chloride solution is added in an amount sufficient to return the treated blood to the patient's systemic iCa level, typically in a range of between about 0.9 mmol/liter and about 1.1 mmol/liter. In another embodiment, determining the amount of calcium chloride solution to be added includes determining a desired calcium mass balance for the patient over a complete dialysis cycle that includes the patient's interdialytic intakes of calcium and liquid, and calculating an intradialytic calcium mass balance, $Ca_{MBHD}$, by obtaining $$Ca_{MBHD} = \left(D_{Ca} \times \left(1 - \frac{Q_f}{Q_e}\right) \times (C_{diCa} - {}_mC_{pCa}) - Q_f \times {}_mC_{pCa}\right) \times t_d \quad (1)$$

wherein:
 $D_{Ca}$ is the dialysance of calcium during the dialysis treatment,
 $Q_f$ is the ultrafiltration rate of blood during the dialysis treatment,
 $Q_e$ is the effective flow rate of blood,
 $C_{diCa}$ is the dialysate inlet concentration of calcium,
 ${}_mC_{pCa}$ is the average serum concentration of calcium in the patient's blood during the dialysis treatment, and
 $t_d$ is the duration of each dialysis treatment.

The calcium concentration in the calcium containing solution is adjusted by calculating $$C_{CaInf} = C_{CaBody} \times \left(\frac{Q_B}{Q_{Inf}}\right) - \left(\frac{Ca_{MBHD}}{Q_{Inf} \times t_d}\right) \quad (2)$$

wherein:
 $C_{CaInf}$ is the concentration of calcium for infusion,
 $C_{CaBody}$ is the concentration of calcium in the patient's body,
 $Q_B$ is the blood flow rate for dialysis,
 $Q_{Inf}$ is the calcium infusion flow rate back to the patient's body,
 $Ca_{MBHD}$ is the calcium mass balance during dialysis treatment, and
 $t_d$ is the duration of each dialysis treatment. See U.S. application Ser. No. 12/580,803.

The extracorporeal blood treatment system 100 further includes means 150, such as extracorporeal blood circuit tubing, for returning treated blood back to the patient. Means 150 can include a large bore dialysis needle, or a separate dialysis access device that connects to the patient's venous system.

In another embodiment, a method of dialyzing blood includes directing blood into a dialysis system including a dialyzer, and directing the blood through a calcium trap located upstream of the dialyzer. The blood can be blood of a patient undergoing dialysis. A typical blood flow rate can be about 300 ml/min. The calcium trap includes a substrate having an immobilized species, the species being adapted to reduce the calcium concentration in the blood to a concentration that prevents blood clotting in the dialysis system, thereby producing calcium-depleted blood. The method further includes directing the calcium-depleted blood through the dialyzer, thereby removing deleterious substances and aqueous fluid from the blood. A typical dialysate flow rate can be about 500 ml/min. The method also includes infusing a calcium containing solution (typically 550 mM $CaCl_2$) into the calcium-depleted blood. Infusing the calcium containing solution can be to adjust a patient's intradialytic calcium mass balance to desired levels. A desired level can be a return of the treated blood to the patient's systemic iCa level, typically in a range of between about 0.9 mmol/liter and about 1.1 mmol/liter, or to another level relative and responsive to the patient's interdialytic intakes of calcium and liquid. The method can further include directing the blood back to the patient.

EXEMPLIFICATION

Calcium Binding Capacity of Alginate

Figure 3:
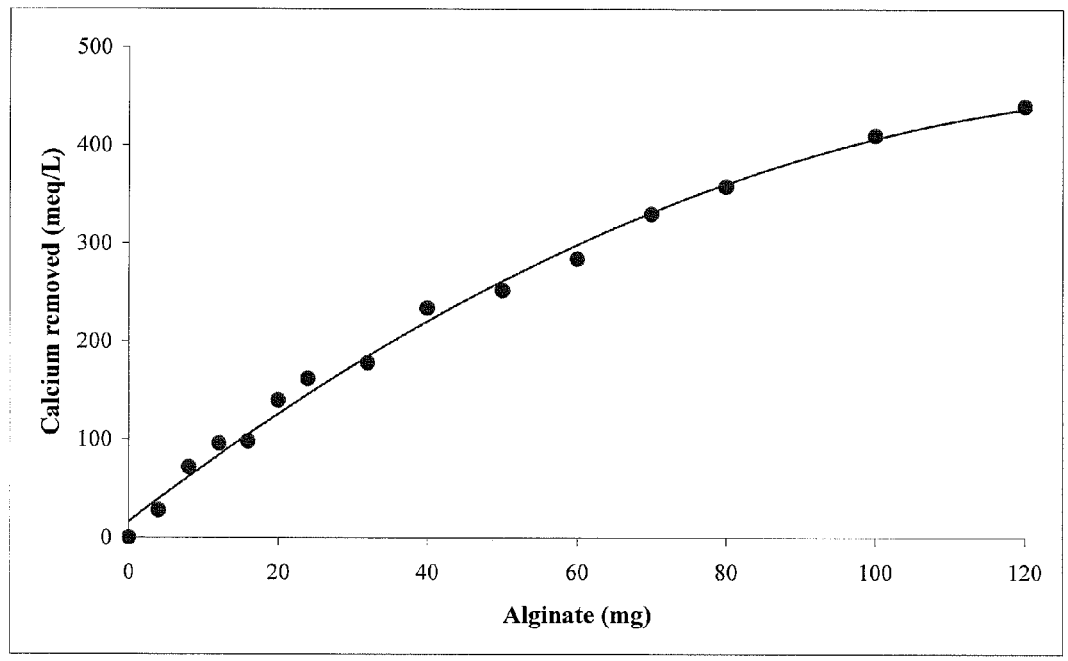
FIG. 3 is a graph of calcium binding capacity (mEq/L) as a function of added mass of alginate (mg).

A 400 mMolar calcium chloride test solution was prepared by dissolving 0.59 grams of $CaCl_2 \cdot 2H_2O$ in 10 ml of reverse osmosis deionized (RO DI) water. A 2% (weight/volume) alginate solution was then prepared by dissolving 0.2 grams of alginate in 10 ml of RO DI water. A hydrogel was formed by adding, drop by drop, the 2% alginate solution into a vial containing 5 ml of 400 mM $CaCl_2$ solution, using a syringe pump (KD Scientific, Inc., Holliston, Mass.), in the following amounts: 0 µl, 200 µl, 400 µl, 600 µl, 800 µl, 1000 µl, 1200 µl, 1600 µl, 2000 µl, 2500 µl, 3000 µl, 3500 µl, 4000 µl, 5000 µl, and 6000 µl. After the alginate solution was added into the $CaCl_2$ solution, the alginate formed beads. The beads were filtered out of solution, and the calcium concentration in the remaining solution was measured by atomic absorption spectrometry. The resulting reduction in calcium concentration from calcium binding to the alginate is shown in FIG. 3 (volume of alginate solution converted to mg alginate), where a fit of the data to an expression of the form $y = -0.02x^2 + 5.9042x + 16.216$ is also shown.

Comparison of Calcium Binding Capacity of Alginate Hydrogels

PLURONIC® alginate hydrogels were prepared by mixing solutions containing one of 2 g of PLURONIC® F68, 1 g of PLURONIC® F68, 2 g PLURONIC® F108, or 1 g PLURONIC® F108, each separately with 1 g of alginate in 100 mL of RO DI water at room temperature for 24 hours to obtain 2% (weight/volume) F68, 1% F68, 2% F108, and 1% F108 alginate hydrogel, respectively, after two electron beam irradiation treatments, for a total electron beam treatment dose of 25 kGy.

Chitosan-alginate hydrogel was prepared by adding 1 g of chitosan into 400 mL of 2% acetic acid until the chitosan was completely dissolved, followed by adding 1 g of alginate into the chitosan solution and mixing at room temperature for 24 hours. The chitosan-alginate hydrogel was then separated by filtration and washed with RO DI water until the pH was greater than about 5.0.

Figure 4:
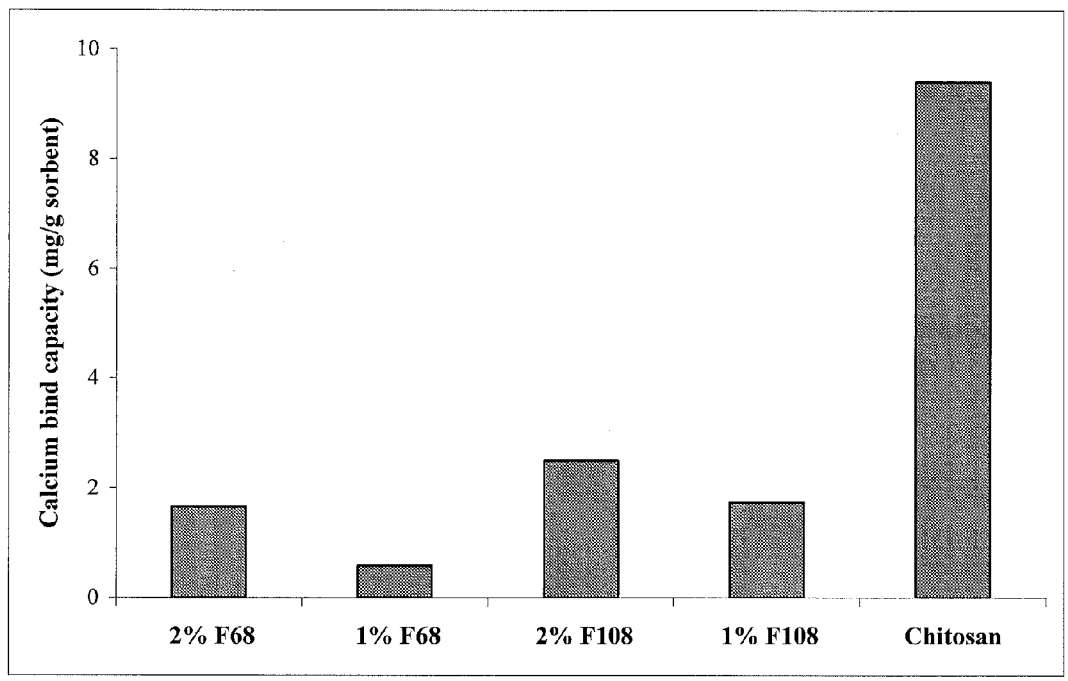
FIG. 4 is a graph of calcium binding capacity (mg/g sorbent) for 2% PLURONIC® F68 (2% F68), 1% PLURONIC® F68 (1% F68), 2% PLURONIC® F108 (2% F108), 1% PLURONIC® F108 (1% F108), and chitosan-alginate hydrogels.

The hydrogels prepared as indicated above were then freeze dried and cut into portions of about 1 mm in maximum dimension. For the calcium binding experiments shown in FIG. 4, 100 mL of 1 mMolar $CaCl_2$ solution were mixed with 1 g of the respective hydrogel in a 100 mL container. The resulting solutions were mixed for 24 hours, and then the containers were spun by centrifuge to separate the hydrogel from the liquid. The remaining calcium in 10 mL of the liquid was analyzed by atomic absorption spectrometry. From the results shown in FIG. 4, the chitosan-alginate hydrogel has the best calcium binding capacity, with about 9.40 mg of calcium removed by 1 g of the chitosan-alginate hydrogel.

Comparison of Calcium Binding Capacity of Chitosan/Alginate Gels in Aqueous Solution and Bovine Heparinized Plasma Aqueous solutions of 50 mL of 1 mMolar calcium chloride ($CaCl_2$) were mixed with the following amounts of chitosan-alginate dry gel: 0.0 g (control), 0.025 g, 0.050 g, 0.100 g, 0.150 g, 0.200 g, 0.250 g, 0.500 g, and 0.750 g. The solutions were mixed for about 24 hours. The calcium concentration in samples from each mixture and a control sample of 1 mMolar $CaCl_2$ was measured by atomic absorption spectrometry.

Solutions of 50 mL of bovine heparinized plasma were mixed with the following amounts of chitosan-alginate dry gel: 0.0 g (control), 0.02 g, 0.04 g, 0.10 g, and 0.2 g. The solutions were mixed for about 3 hours. The calcium concentration in samples from each mixture was measured by a calcium analysis kit (BioAssay Systems, Hayward, Calif.).

Figure 5:
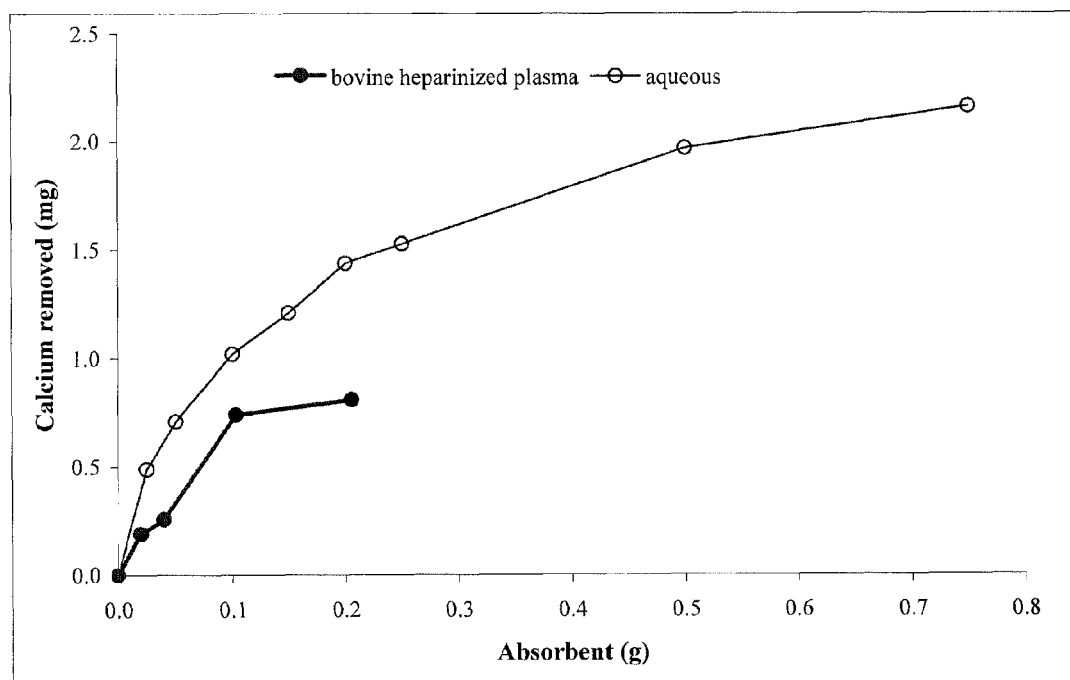
FIG. 5 is a graph of calcium removed (mg) as a function of absorbent (g) from bovine heparinized plasma and from aqueous solution.

As shown in FIG. 5, the calcium binding ability of the chitosan-alginate is about 50% lower in bovine heparinized plasma than in aqueous solution.

The relevant teachings of all patents, published patent applications, and literature references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An extracorporeal blood treatment system comprising:
means for withdrawing blood from a patient;
means for transporting the blood through a calcium trap, the calcium trap including a substrate comprising chitosan and having an immobilized species, the species comprising alginate and being adapted to reduce the calcium concentration in the blood to a concentration that prevents blood clotting in the extracorporeal blood treatment system, thereby producing calcium-depleted blood;
means for treating the calcium-depleted blood downstream of the calcium trap by an extracorporeal blood treatment device, thereby producing treated calcium-depleted blood;
means for infusing calcium into the treated calcium-depleted blood downstream of the extracorporeal blood treatment device to add calcium to the treated calcium-depleted blood; and
means for returning treated blood back to the patient.

2. The extracorporeal blood treatment system of claim 1, wherein the substrate in the calcium trap comprises hydrogel beads.

3. The extracorporeal blood treatment system of claim 2, wherein the hydrogel beads include chitosan.

4. The extracorporeal blood treatment system of claim 1, wherein the extracorporeal blood treatment device includes dialysis, adsorption, and filtration.

5. The extracorporeal blood treatment system of claim 1, further including a dialyzer, the dialyzer including a hydrophobic membrane wherein at least one copolymer is attached to the hydrophobic membrane, and wherein each copolymer is comprised of at least one hydrophobic segment and at least one hydrophilic segment.

6. The extracorporeal blood treatment system of claim 1, wherein calcium is added to the calcium-depleted blood to adjust the patient's intradialytic calcium mass balance to desired levels relative to the patient's interdialytic intakes of calcium and liquid.

7. In a system for dialyzing blood of a patient having an inlet for introducing blood of the patient, a dialyzer for dialyzing blood, a calcium infusion device downstream of the dialyzer to add calcium to the calcium-depleted blood, and an outlet for discharging dialyzed blood back to the patient, the improvement comprising providing a calcium trap upstream of the dialyzer including a substrate comprising chitosan and having an immobilized species, the species comprising alginate and being adapted to reduce the calcium concentration in the blood to a concentration that prevents blood clotting in the system.

8. The improvement of claim 7, wherein the substrate in the calcium trap comprises hydrogel beads.

9. The improvement of claim 8, wherein the hydrogel beads include chitosan.

10. The improvement of claim 7, wherein the dialyzer includes a hydrophobic membrane with at least one copolymer attached to the hydrophobic membrane, and wherein each copolymer is comprised of at least one hydrophobic segment and at least one hydrophilic segment.

11. The improvement of claim 7, wherein the calcium infusion device is adapted to adjust the patient's intradialytic calcium mass balance to desired levels relative to the patient's interdialytic intakes of calcium and liquid.

12. A method of dialyzing blood comprising:
a) directing blood into a dialysis system including a dialyzer;
b) directing the blood through a calcium trap located upstream of the dialyzer, the calcium trap including a substrate comprising chitosan and having an immobilized species, the species comprising alginate and being adapted to reduce the calcium concentration in the blood to a concentration that prevents blood clotting in the dialysis system, thereby producing calcium-depleted blood;
c) directing the calcium-depleted blood through the dialyzer, thereby removing deleterious substances and aqueous fluid from the blood; and
d) infusing a calcium containing solution into the calcium-depleted blood.

13. The method of dialyzing blood of claim 12, wherein the substrate in the calcium trap comprises hydrogel beads.

14. The method of dialyzing blood of claim 13, wherein the hydrogel beads include chitosan.

15. The method of dialyzing blood of claim 12, wherein the dialyzer includes a hydrophobic membrane with at least one copolymer attached to the hydrophobic membrane, and wherein each copolymer is comprised of at least one hydrophobic segment and at least one hydrophilic segment.

16. The extracorporeal blood treatment system of claim 3, wherein the chitosan is crosslinked chitosan or positively charged chitosan, or a combination thereof.

17. The improvement of claim 9, wherein the chitosan is crosslinked chitosan or positively charged chitosan, or a combination thereof.

18. The method of claim 14, wherein the chitosan is crosslinked chitosan or positively charged chitosan, or a combination thereof.

* * * * *